(12) United States Patent
Gauchet

(10) Patent No.: US 6,582,466 B1
(45) Date of Patent: Jun. 24, 2003

(54) INTERVERTEBRAL DISC PROSTHESIS WITH REDUCED FRICTION

(75) Inventor: Fabien Gauchet, Duvy (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/857,656

(22) PCT Filed: Dec. 9, 1999

(86) PCT No.: PCT/FR99/03070

§ 371 (c)(1),
(2), (4) Date: Jun. 7, 2001

(87) PCT Pub. No.: WO00/35382

PCT Pub. Date: Jun. 22, 2000

(30) Foreign Application Priority Data

Dec. 11, 1998 (FR) .............................................. 98 15669

(51) Int. Cl.$^7$ .................................................. A61F 2/94
(52) U.S. Cl. ................................. 623/17.11; 623/17.12; 606/61
(58) Field of Search ........................... 623/17.11, 17.12, 623/18.11; 606/60, 61

(56) References Cited

U.S. PATENT DOCUMENTS

| 4,932,969 A | 6/1990 | Frey et al. ..................... 623/17 |
| 5,674,294 A | 10/1997 | Bainville et al. ............ 101/148 |
| 6,187,043 B1 * | 2/2001 | Ledergerber .................... 623/8 |

FOREIGN PATENT DOCUMENTS

| DE | 3939593 | 6/1991 |
| FR | 2723841 | 3/1996 |
| FR | 2728037 | 6/1996 |

* cited by examiner

Primary Examiner—Michael A. Brown
(74) Attorney, Agent, or Firm—Lerner, David, Littenberg, Krumholz & Mentlik, LLP

(57) ABSTRACT

An intervertebral disc prosthesis includes two opposing plates, a flexible seal extending between the two plates for forming a fluid-tight chamber between the two plates, a first fluid provided in the chamber, and a compressible body provided in the first fluid in the chamber, whereby the compressible body has greater resistance to compression forces than the first fluid.

21 Claims, 2 Drawing Sheets

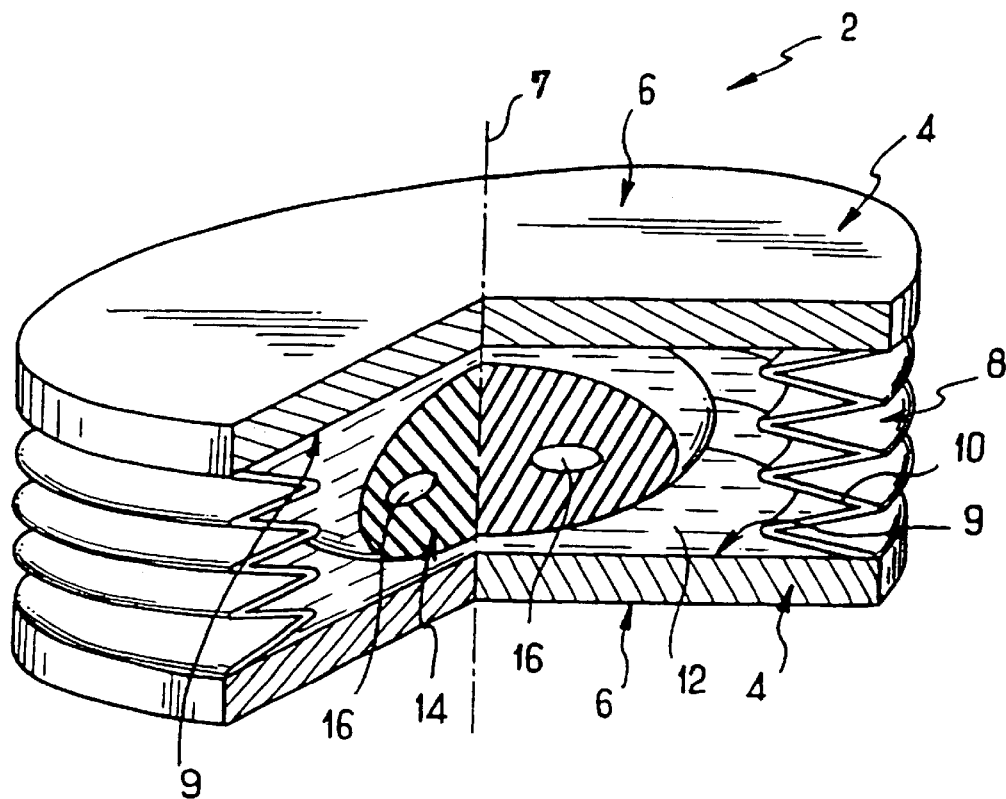
FIG_1
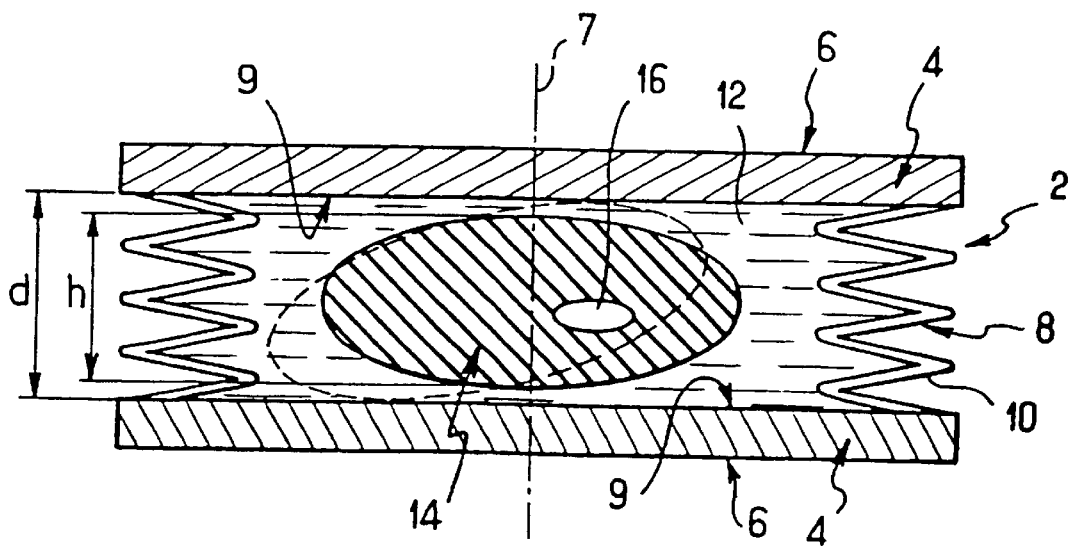
FIG_2

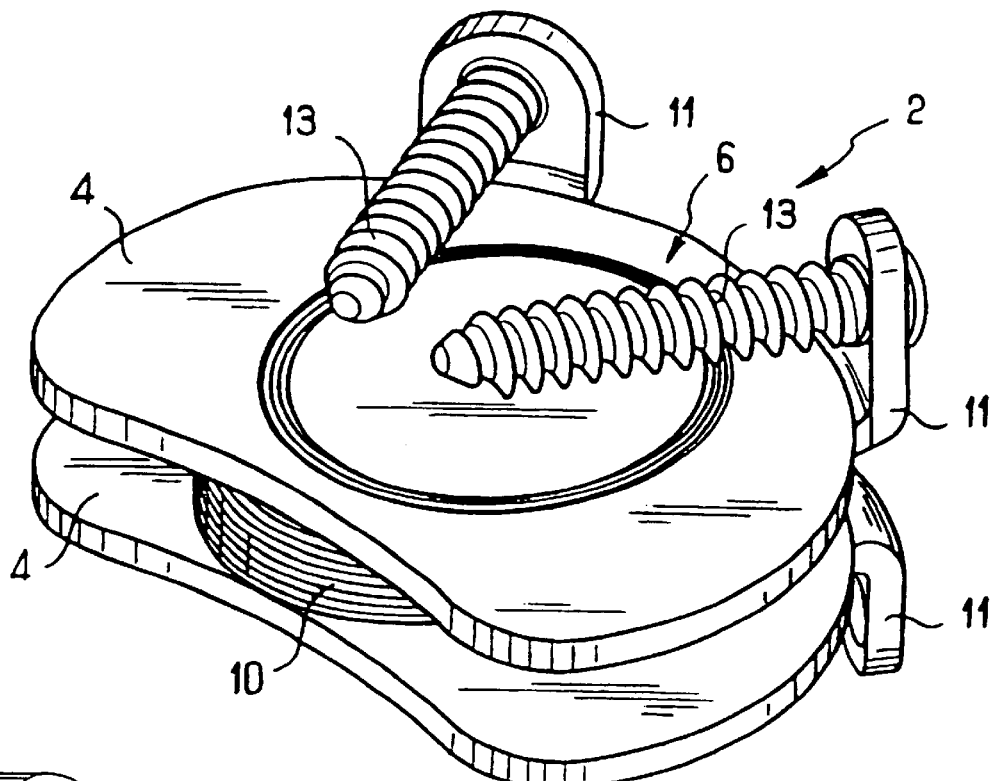
FIG_3
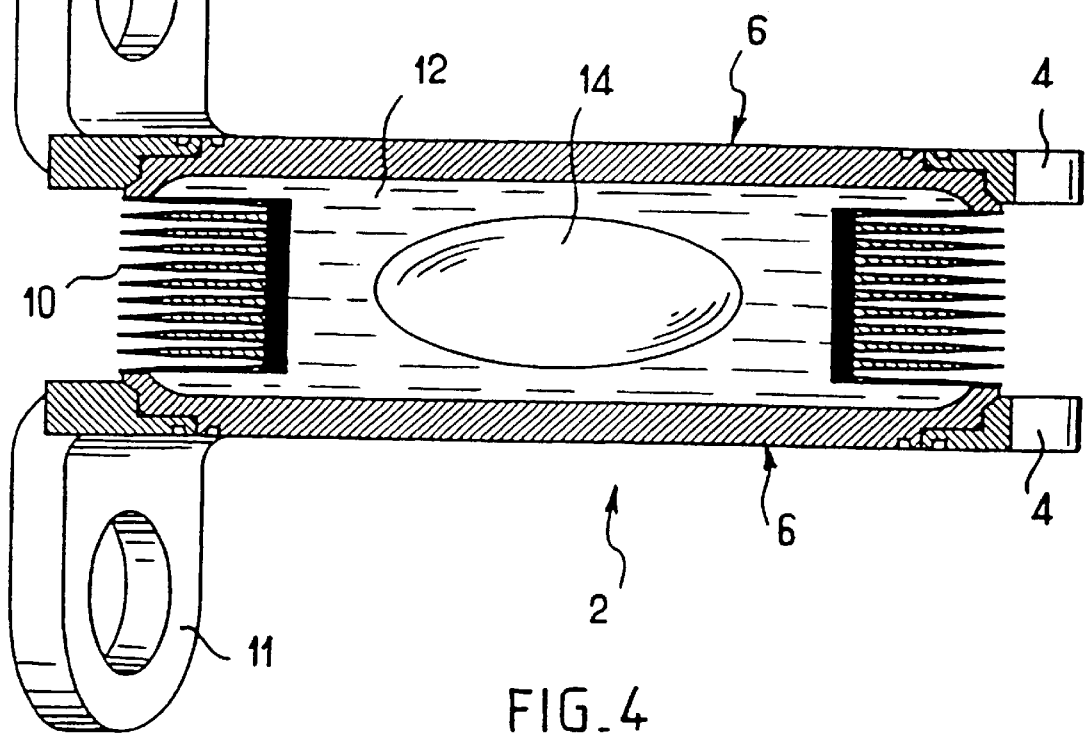
FIG_4

INTERVERTEBRAL DISC PROSTHESIS WITH REDUCED FRICTION

The invention concerns intervertebral disc prostheses.

The document EP-0,277,282 discloses such a prosthesis comprising two plates which are intended to come into contact with the vertebral plates of the vertebrae adjacent to the disc which is to be replaced, and a cushion interposed between the plates and comprising a compressible body forming a chamber for a liquid. However, wear can occur between the compressible body and the plates, leading in particular to the emission of solid particles and to their dispersion in the human body. Moreover, although the mechanical behavior of this prosthesis comes close to that of a healthy natural intervertebral disc, it is desired to make available a prosthesis which in a different way comes close, or even closer, to the behavior of a normal disc.

It is an object of the invention to make available a prosthesis which generates less wear and which has different mechanical behavior.

With a view to achieving this object, the invention provides an intervertebral disc prosthesis comprising two plates, and a cushion interposed between the plates and having a chamber filled with fluid and a compressible body, where the body is so shaped as to be able to take up a position in which it is in contact with at most one of the plates when the prosthesis is subjected to compression tending to bring the plates closer to each other.

This compression will be able to have an intensity equal to 3000 N.

The invention also provides an intervertebral disc prosthesis comprising two plates, and a cushion interposed between the plates and having a chamber filled with fluid and a compressible body, where the body is so shaped as to be able to take up a position in which it is in contact with at most one of the plates when the prosthesis is not stressed.

Thus, the body is in contact with at most one of the two plates, or with neither of them. This therefore reduces the friction between the body and the plates, and also the wear and the generation of particles.

The body is advantageously immersed in the fluid.

The body is advantageously movable relative to each plate.

This characteristic further reduces the probability of friction between the body and the plates, as the body spontaneously arranges itself in a position in which it is stressed to the least possible extent by the plates.

The fluid is advantageously compressible.

Thus, the stresses created by the relative movements of the plates are not only returned across the whole surface of the body and in all directions by the fluid. Said fluid also takes up some of these stresses itself, the remainder of said stresses being taken up by the compressible body.

The fluid advantageously has a resistance to compression less than that of the body.

The body advantageously has at least one cell isolated from the outside of the body.

The presence of one or more cells influences the mechanical behavior of the compressible body over and above the choice of the material and its dimensions.

The cell is advantageously filled with a second fluid.

When the prosthesis is unstressed, the second fluid advantageously has a pressure greater than or equal to that of the fluid in the chamber.

Other characteristics and advantages of the invention will become more apparent from the following description of a preferred embodiment which is given as a nonlimiting example. In the attached drawings:

FIG. 1 is a perspective and partially cutaway view of a preferred embodiment of the prosthesis;

FIG. 2 is a view showing the prosthesis from FIG. 1 in axial section;

FIG. 3 is a perspective view of an alternative embodiment of the prosthesis; and FIG. 4 is a view showing the prosthesis from FIG. 3 in axial section.

Referring to FIGS. 1 and 2, the intervertebral disc prosthesis 2 is here preferably intended for the lumbar region of the spine. It comprises two plates 4 of generally planar shape which have been illustrated as having a plane of discoid shape but which will preferably have a bean shape with posterior hilum, as is illustrated in the alternative embodiment in FIGS. 3 and 4. The two plates 4 extend parallel to each other and facing each other. Although not illustrated in FIGS. 1 and 2, but shown in the alternative embodiment in FIGS. 3 and 4, each plate can comprise, on its outer face 6 remote from the other plate, at least one securing lug 11 which projects from this face and which has an orifice for the passage of a bone screw 13 for anchoring it in the vertebra in contact with this plate. Each plate 4 is here made of titanium or titanium alloy. The plates have a common axis 7 constituting a main axis of the prosthesis perpendicular to the plates.

For short-term anchoring of the disc prosthesis 2 in the column, the screws 13 can be anchored in the body of the vertebrae adjacent to the disc which is to be replaced.

However, it will be possible to provide for long-term anchoring in which, in addition, the surfaces 6 of the plates 4 in contact with the adjacent vertebrae are covered with hydroxyapatite or any other substance known per se for stimulating bone growth. Before being covered, said surfaces 6 can be treated to obtain a more or less porous surface condition, with anchoring points for the bone tissue, so as to ensure a better interface with said bone tissue.

The prosthesis has a cushion or intermediate part 8 interposed between the plates. The cushion 8 comprises a chamber 10 which is here formed by a bellows. The bellows has a shape which is symmetrical in revolution about the axis 7. Its wall profile comprises corrugations which make it possible to vary the length of the bellows 10 in the axial direction 7 without appreciably varying the surface area of its cross section transverse to the axis 7. In this case the bellows is made of titanium or titanium alloy so that it has a certain degree of axial strength and forms a compression spring. It can also be deformed in a direction perpendicular to the axis 7 or be subjected to torsion about the axis 7 or any axis perpendicular thereto. At its two axial ends, the bellows 10 has edges which are bonded to respective edges of the plates 4 projecting, for example as is illustrated in FIGS. 3 and 4, from an inner face 9 of the plates. Said bonding is made leaktight so that the bellows 10 and the two plates 4 define a leaktight chamber.

The bellows 10 can have ten convolutions, that is to say eight outer crests in addition to the two crests attached to the plates. It has here an external diameter of about 30 mm and an internal diameter of about 17 mm. Its height, when the prosthesis is not loaded, is 10 mm. The wall of the bellows can be made using one, two or three sheets each measuring 0.1 mm in thickness and of which the sum of the thicknesses forms the thickness of the wall. The bellows here has an inherent strength of about 1.6 N/mm.

The chamber defined by the plates 4 and the bellows 10 encloses a fluid 12 which is in this case compressible and biocompatible. This is a mixture of a liquid and of a gas which is partially soluble in the liquid. The fluid 12 is in direct contact with the plates 4 and the bellows 10. The liquid can be water or a physiological saline.

The cushion 8 also comprises, in addition to the fluid 12, a compressible body 14 which can be made of an elastically compressible material such as an elastomer, or a viscoelastic material such as silicone, as is the case here.

The body 14 here has the shape of an ellipsoid which has been flattened on its axis about which it has a symmetry of revolution, said axis coinciding with the axis 7 in the figures. The smallest overall height of the body 14 measured on its axis of revolution will be called "h". This distance will not necessarily be measured parallel to the main axis 7 of the prosthesis since the body 14 can be inclined such that its axis of symmetry is inclined relative to the main axis 7 of the prosthesis, as is illustrated by dashes in FIG. 2. This value h is instantaneous. It is variable depending on circumstances since the body 14 is compressible, in particular on its axis of symmetry. The body moreover has another overall dimension greater than h, and measured in a plane perpendicular to its axis of symmetry. The instantaneous distance separating the centers of the two plates 4 from each other will be called "d". This value too is instantaneous, since the distance between the two centers can vary when the prosthesis is compressed. This value is again measured on the main axis 7 of the prosthesis.

The prosthesis can undergo compression on the main axis 7, tending to bring the two plates 4 closer to each other, without modifying their relative inclination. It can also undergo flexion about any axis perpendicular to the main axis 7 and tending to incline the plates relative to each other and thus bring a part of their peripheral edges closer together. These movements are the main ones likely to modify the distance between the plates: the shearing movements tending to relatively displace the plates 4 parallel to their plane, and the movements of relative rotation of the plates about the axis 7 do not modify the distance between the plates to any significant extent.

The prosthesis is configured in such a way that, irrespective of the circumstances, in particular irrespective of the stresses which the prosthesis undergoes and the deformation which it presents, the body 14 can always spontaneously take up a position in which it is in contact with at most one of the plates 4, or neither of them. Such a position can be an inclined position in which the axis of symmetry of the body 14 is inclined relative to the main axis 7 and/or in which the body is offcentered in relation to this axis, as is illustrated by dashes in FIG. 2, or else a position in which the axis of symmetry of the body coincides with the main axis 7 of the prosthesis. This property results principally from the choice of the a shape and dimensions of the body 14, the volume of the chamber of fluid 12, and the compressibility of the body 14 and the fluid 12. In this case, this property of the body is obtained all the more easily as the body 14 is immersed in the fluid 12 and is totally movable relative to each of the plates 4 without any anchoring to them. The person skilled in the art will have no difficulty in making prostheses which function in this way. This property of the body 14 will of course apply when the prosthesis is unstressed, that is to say before it is fitted on the patient. It will also apply after fitting, under the conditions of use. For example, it will be possible to ensure that this property applies for any compression stressing of the prosthesis up to an intensity of 3000 N, which corresponds to an intensity sometimes withstood by a healthy natural disc, for example when the patient is bearing a load. For safety reasons, this limit may be extended to an intensity of 5000 N, which intensity corresponds to the limit of resistance of the actual vertebrae.

When the smallest overall dimension h of the body 14 is, at rest, only slightly less than the distance d separating the centers of the plates, as is the case in the figures, it will be preferable to provide for the possibility of substantial lateral clearance of the body 14 in the chamber. For example, the dimension of the chamber perpendicular to the main axis 7 will be between 1.3 and 1.5 times the greatest overall dimension of the body 14 in the same direction.

The body 14 here comprises a number of cells 16 which are closed and are isolated from the outside of the body 14. Each cell encloses a fluid which is here a gas having a pressure greater than the pressure of the fluid 12 in the chamber when the prosthesis is at rest. These cells 16 modify the behavior of the body 14 under compression, particularly by locally reducing its compressibility. The cells may or may not be in communication with one another.

The ellipsoid shape of the body 14 is particularly advantageous since it makes it possible to give the body a large volume and a large area of surface contact with the fluid 12 in the chamber while at the same time giving it a small dimension h and permitting substantial relative movements of the plates both in compression and in flexion.

The alternative embodiment in FIGS. 3 and 4 comprises a cushion analogous to that in FIGS. 1 and 2.

Many modifications can of course be made to the invention without departing from the scope thereof.

The body 14 can be fixed to one of the plates 4, the prosthesis being arranged so that the other plate 4 cannot come into contact with the body 14.

The body 14 can have different shapes, for example a spherical shape.

The bellows can have an elliptic shape in cross section.

The fluid 12 can be a liquid.

In this case, this liquid, and the material of the body 14, will be able to be chosen so that the liquid does not wet this material even though it can come into contact with it. Such a property implies that it is necessary to supply a certain energy in order to produce this contact, which energy is restored when it ceases to be supplied. This spring effect is all the more appreciable when the body is porous. When the pores constitute long networks, the dissipation of energy produced upon circulation of the liquid entering or leaving the pores produces a damping effect which combines with the spring effect to give a hysteresis form to the curve illustrating the intensity of compression undergone by the prosthesis as a function of the variation in the distance d.

What is claimed is:

1. An intervertebral disc prosthesis comprising:
   two opposing plates;
   a flexible seal extending between said two plates for forming a fluid-tight chamber between said two plates;
   a first compressible fluid provided in said chamber;
   a compressible body provided in said first compressible fluid in said chamber, wherein said compressible body has greater resistance to compression forces than said first compressible fluid.

2. The intervertebral disc prosthesis as claimed in claim 1, further comprising at least one cell inside said compressible body, wherein said at least one cell is filled with a second fluid.

3. The intervertebral disc prosthesis as claimed in claim 2, wherein said second fluid is a gas.

4. The intervertebral disc prosthesis as claimed in claim 2, wherein said at least one cell is adapted to locally reduce compressibility of said compressible body.

5. The intervertebral disc prosthesis as claimed in claim 2, wherein said first compressible fluid in said chamber has a first pressure level and said second fluid in said at least one cell has a second pressure level, the second pressure level is greater than or equal to the first pressure level when said prosthesis is unstressed.

6. The intervertebral disc prosthesis as claimed in claim 1, wherein said flexible seal includes a bellows structure.

7. The intervertebral disc prosthesis as claimed in claim 6, wherein said bellows has an upper edge attached to a first one of said two plates and a lower edge attached to a second one of said two plates.

8. The intervertebral disc prosthesis as claimed in claim 1, wherein said first fluid is biocompatible.

9. The intervertebral disc prosthesis as claimed in claim 8, wherein said first fluid includes a liquid and a gas.

10. The intervertebral disc prosthesis as claimed in claim 1, wherein said compressible body comprises an elastically compressible material.

11. The intervertebral disc prosthesis as claimed in claim 1, wherein said compressible material comprises materials selected from the group consisting of elastomers, viscoelastic materials and silicones.

12. The intervertebral disc prosthesis as claimed in claim 1, wherein said compressible body has a substantially ellipsoidal or spherical shape.

13. The intervertebral disc prosthesis as claimed in claim 1, wherein said two plates are movable relative to one another.

14. The intervertebral disc prosthesis as claimed in claim 1, wherein at least one of said two plates includes a securing element for securing the at least one of said two plates to vertebral bone.

15. The intervertebral disc prosthesis as claimed in claim 1, wherein said compressible body is movable within said compressible first fluid and relative to said two plates.

16. An intervertebral disc prosthesis comprising:

two opposing plates;

a flexible seal extending between said two plates for forming a fluid-tight chamber between said two plates;

a compressible first fluid provided in said chamber;

a compressible body provided in said chamber, wherein said compressible body has at least one cell embedded therein filled with a second fluid.

17. The intervertebral disc prosthesis as claimed in claim 16, wherein said at least one cell is adapted to locally reduce compressibility of said compressible body.

18. The intervertebral disc prosthesis as claimed in claim 16, wherein said compressible first fluid in said chamber has a first pressure level and said second fluid in said at least one cell has a second pressure level that is greater than or equal to the first pressure level of said compressible fluid when said prosthesis is unstressed.

19. The intervertebral disc prosthesis as claimed in claim 16, wherein said flexible seal includes a bellows structure having an upper edge attached to a first one of said two plates and a lower edge attached to a second one of said two plates.

20. The intervertebral disc prosthesis as claimed in claim 16, wherein said first fluid is biocompatible and includes a liquid and a gas.

21. The intervertebral disc prosthesis as claimed in claim 16, wherein said compressible body has a substantially ellipsoidal or spherical shape.

* * * * *